United States Patent [19]

Buinicky et al.

[11] 4,101,560

[45] Jul. 18, 1978

[54] SHAPED, BONDED BORIDE CATALYSTS

[75] Inventors: Ernest P. Buinicky, Newburgh; Joseph A. Durkin, Fishkill; John H. Estes, Wappingers Falls, all of N.Y.

[73] Assignee: Texaco Inc., New York, N.Y.

[21] Appl. No.: 760,779

[22] Filed: Jan. 19, 1977

Related U.S. Application Data

[62] Division of Ser. No. 656,048, Feb. 6, 1976, Pat. No. 4,033,901.

[51] Int. Cl.$^2$ .................................................. C07D 301/20
[52] U.S. Cl. ................................................. 260/348.29
[58] Field of Search ...................... 260/348.5 L, 348.29

[56] References Cited

U.S. PATENT DOCUMENTS

| | | | |
|---|---|---|---|
| 3,398,199 | 8/1968 | Walde | 252/432 |
| 3,836,452 | 9/1974 | Gleim | 252/432 |

OTHER PUBLICATIONS

Mashio, F. et al., Mem. Fac. Ind. Arts Kyoto Tech. Univ., Sci. Technol., (1967), No. 16, pp. 79-82, 89-91.

*Primary Examiner*—Norma S. Milestone
*Attorney, Agent, or Firm*—Thomas H. Whaley; Carl G. Ries; Henry W. Archer

[57] ABSTRACT

Disclosed is a shaped catalyst composed of finely divided particles of binary or ternary boride compounds having the general formula $M_xB_y$ or $M_xB_yR_z$ wherein $x$ is an integer from 1-5; $y$ is an integer from 1-2; $z$ is an integer from 1-4; B is boron; M is an element selected from the groups II-A, III-B, IV-B, V-B, VI-B, VII-B, VIII, III-A, IV-A, and V-A of the Periodic Table, the rare earths, and the actinides; R is an element different from M selected from the same group of elements in the Periodic Table as M; the particles being bonded by 1 to 10% by weight of finely divided particles of preoxidized aluminum, zinc, or magnesium. The preferred catalyst materials are those boron-containing substances which are substantially insoluble in the reaction mixture containing the organic hydroperoxides olefins and products and which are bonded by heat treated aluminum particles having an oxide coating constituting from 5 to 10 percent of the particles.

Also disclosed is a method for the liquid phase epoxidation of an olefinic compound with an organic hydroperoxide at temperatures of about 90 to 130° C at a pressure sufficient to maintain the mixture substantially in liquid phase in the presence of a catalytically effective amount of the novel catalyst material.

3 Claims, No Drawings

SHAPED, BONDED BORIDE CATALYSTS

This is a division of application Ser. No. 656,048 filed Feb. 6, 1976, now U.S. Pat. No. 4,033,901 issued July 5, 1977.

BACKGROUND OF THE INVENTION

1. Field of the Invention

This invention relates to catalysts for expediting the oxidation of an olefin to the corresponding oxirane; and, more particularly to a shaped and metal-bound catalyst of a boron-containing substance for catalyzing the liquid phase epoxidation of olefins with organic hydroperoxides.

2. Statement of the Prior Art

Oxiranes or epoxides, while being valuable commercial products in and of themselves, are also commercially valuable as starting reactants for synthesizing many useful compounds such as polyether polyols for urethane systems. Over the years many methods have been disclosed for synthesizing such compounds. The majority of these methods involves the oxidation of the corresponding olefin. For example, it is known that ethylene can be converted to the corresponding epoxide by a vapor phase partial oxidation with molecular oxygen over a silver catalyst. However, the ease of olefin oxidation varies greatly depending upon the size and structure of the olefinic starting reactant and therefore many of the disclosed processes are not effective for epoxidizing olefins in general.

Recently it has been disclosed that olefinically unsaturated organic compounds can be oxidized to the corresponding oxirane compound in liquid phase with organic hydroperoxides in the presence of various catalysts.

Various tungsten catalysts, their preparation and uses are described in Ind. Eng. Chem. 57 (9), 53–60 where the conversion of olefinic double bonds is described as requiring high concentrations of the olefin reactant and of the tungsten catalyst. In particular, the article describes the epoxidation of allyl alcohol in water using 1.2–2.0 allyl alcohol and 15–40 water to 1.0 of hydrogen peroxide, with a catalyst concentration of about 4 grams/mole of $H_2O_2$; these catalysts being tungstic acid, phosphotungstic acid or their salts.

The same article also mentions that suitable tungsten catalysts may be prepared by pelleting tungstic acid with 2% graphite as a lubricant at high pressures of up to 62 tons per square inch.

More recently it has been disclosed in U.S. Pat. No. 3,832,363 that the epoxidation of an ethylenic compound to the corresponding oxirane compound is catalyzed by the presence of a boron oxide, a dehydrated boric acid and the hydrocarbyl esters thereof. The compounds disclosed in this patent which are useful as catalysts contain at least one B-O-B linkage.

The previously described catalysts suffer from one or more disadvantages when employed in liquid phase epoxation. For example, many of the previously known catalysts materials are expensive and difficult to prepare and/or difficult to use, requiring special apparatus or highly selective reaction conditions and/or being limited to heterogeneous or homogeneous type reaction systems.

In coassigned copending U.S. patent application Ser. No. 569,004 filed Apr. 4, 1975, are disclosed binary and ternary boride compounds consisting of boron and at least one element selected from groups II-A, III-B, IV-B, V-B, VI-B, VII-B, VIII, III-A, IV-A and V-A of the Periodic Table, the rare earths and the actinides. No particular binders are disclosed in that application for forming shaped catalytic materials, but to carry out expoxidation using tubular reactor technology, it is necessary that the catalysts be shapes and not powders. However, certain binders can cause loss of catalytic activity.

SUMMARY OF THE INVENTION

The invention comprises a shaped catalytic material composed of finely divided particles of a boron-containing compound useful for the epoxidation of an olefin with an organic hydroperoxide and at least one element selected from groups II-A, III-B, IV-B, V-B, VI-B, VII-B, VIII, III-A, IV-A, and V-A of the Periodic Table, the rare earths, and the actinides; bonded by 1 to 10% by weight of finely divided particles of preoxidized aluminum, zinc or magnesium, the catalyst being subjected to a pressure from about 25 to 40 tons/sq. in. (and preferably heated to 520° C ± 50° F for Al, 350° C ± 30° F for Zn and 500° F to ± degrees for Mg) in an inert gas to improve the crush strength of the shapes. The present catalysts are shaped binary borides and ternary borides having the general formula respectively $M_xB_y$ and $M_xB_yR_2$ wherein $x$ is an integer from 1 to 5; $y$ is an integer from 1 to 12; $z$ is an integer from 1 to 4; B is boron; M is a single element selected from the above grouping and R is an element selected from the above grouping but different from M, the particles of boride material being bonded by aluminum, magnesium or zinc.

According to a preferred embodiment, the shaped catalyst is heat treated in an inert atmosphere to increase its crush strength.

According to a process aspect of the invention, the epoxidation of an olefinically unsaturated compound to a corresponding oxirane derivative employing organic hydroperoxides as epoxidizing agents is carried out in the presence of a catalytic amount of the boron containing substances at low temperatures under liquid phase conditions.

DETAILED DESCRIPTION OF THE PREFERRED EMBODIMENT

The catalyst materials in accordance with a preferred embodiment are those boron-containing substances which are not substantially dissolved or attacked by the reactants or product mixtures under the reaction conditions encountered by the epoxidation of olefinic compound to the corresponding oxirane with organic hydroperoxide. These catalyst materials may be generally employed in the liquid phase heterogeneous epoxidation systems wherein organic compounds having at least one aliphatic olefinically unsaturated carbon-carbon bond and from 2 to 60 carbon atoms are oxidized with an organic hydroperoxide.

Catalyst Materials

The catalysts used within the scope of the instant invention are generally boron containing materials effective in catalyzing the liquid phase epoxidation of an olefin with an organic hydroperoxide. These materials are characterized as boride compounds of boron and at least one element selected from group II-A, III-B, IV-B, V-B, VI-B, VII-B, VIII, III-A, IV-A and V-A of the Periodic Table, the rare earth and the actinides. More particularly these boride compounds may be either the so-called binary borides or the ternary borides. The binary borides may be represented by the general formula $M_xB_y$ wherein B is boron; M is an element selected as above; x is an integer from 1 to 5; B is boron and y is an integer from 1 to 12. The ternary borides may be represented by the general formula $M_xB_yR_z$ wherein M, x, B and y represent elements or integers as described herein above, R is an element selected from the same periodic groupings as M but is an element different from M in any given compound and z is an integer from 1 to 5. These materials preferably are 1 to 10 micron sized powders of low surface area and are shaped into bonded pellets of 5/32 inch diameter in a pelletizing machine at a pressure of from 25 to 50 tons/sq. in.

The preferred catalytic materials are the binary borides. The borides binary boride compounds are those catalysts which are not dissolved or attacked by the reaction mixtures containing the organic hydroperoxides, olefins, and products. The preferred catalytic materials thus form substantially heterogeneous systems with the liquid reactants and products. Preferred catalysts are $LaB_6$, $CeB_6$, $ZrB_2$, NbB, WB, $W_2B_5$, MnB, NiB, $AlB_2$, and $AlB_{12}$. Other examples of boride compounds useful as insoluble catalysts are $CaB_6$, $TiB_2$, $ZrB_{12}$, $HfB_2$, $TaB_2$, FeB, $Co_3B$, $Co_2B$, CoB, $SiB_4$, $SiB_6$, and $B_4C$.

It should be noted that the empirical formulas given herein do not necessarily represent the exact stoichiometry of the catalytic material but rather represent particular crystalline phases which may be nonstoichiometric due to lattice defects, vacant sites and the like. It is intended that the scope of the instant invention cover all of formed shapes so-called binary and ternary borides represented by the formulas set out herein above, which include but are not limited to borides having isolated boron atoms such as for example $M_4B$, $M_3B$, $M_2B$, $M_5B_2$ and $M_7B_3$; borides having single and double chains of boron atoms, i.e. those crystalline structures where a boron, boron linkage exist such as $M_3B_2$ and $M_4B_3$ and $M_3B_4$; borides having two dimensional nets such as those represented by the formula $MB_2$ and $M_2B_5$; and borides having a three dimensional boron network such as those having the formulas $MB_4$, $MB_6$, and $MB_{12}$.

As used herein, solubility and insolubility are relative terms. That is, those boron containing compounds which are characterized as forming heterogeneous systems may be in fact somewhat soluble in the reaction mixture. Likewise, so-called soluble boron containing substances may not form a completely homogeneous single phase with the reactants and reaction products. When utilizing the so-called soluble boron containing substances, it is preferable that sufficient catalyst be used to create a heterogeneous system.

Additionally, it will be realized by those skilled in the art that mixtures of one or more of the boride catalytic material may be used to provide, for example, selectivity in epoxidizing certain olefinic compounds.

BINDERS

As noted above, the metal binders of the invention include preoxidized aluminum, magnesium and zinc. Obviously, certain binders will be preferred with certain catalytic compositions and will be found to enhance their activities. Only preoxidized binders will form a free flowing mixture with the boride which will release well from a mold or shaping device to give shapes having a metallic sheen and sufficient porosity. If unoxidized binders used, mixtures thereof with borides do not flow easily into dies when shaping, such as pill making is attempted, the binders extend into the space between the die and the punch jamming the maching and breaking the punches. On the basis of studies of electron micrographs of binder particles volumes and other analysis, it has been established that an oxide coating on the binder particles of between 5 and 10 percent of the volume of the particles is required.

Various methods of providing such coating will occur to those skilled in the art. One suitable method involves exposing the binder powder to moist air in a fluidized mold at 200° to 250° F until the weight gain of the powder corresponds to the 5 to 10% conversion.

Olefinically Unsaturated Reactants

The olefinically unsaturated materials which can be epoxidized in accordance with the invention are generally organic compounds having at least one aliphatic olefinically unsaturated carbon-carbon double bond containing from 2 to about 60 carbon atoms. In fact there are no known olefinically unsaturated organic compound which cannot be utilized within the scope of the instant invention. For example, the olefinic reactant may be of acylic, monocyclic, bicyclic, or polycyclic olefin and may be of a monoolefin, or a polyolefin. Additionally, the olefinic linkages of the polyolefins may be conjugated or nonconjugated. Further, the olefinic reactant may be a hydrocarbon or a substituted hydrocarbon with functional groups containing, for example oxygen, halogen, nitrogen, or sulfur. Typical substituted functional groups are hydroxy groups; ether groups; ester groups; halogens such as chlorine and flourine, nitrile groups, amide groups; sulfur containing groups nitrate groups; and the like. Examples of suitable olefinic reactants include ethylene, propylene, isobutylene, hexene-2-, octene-1, eicosene-1, pipyrlene, vinylcyclohexene, dicoclopentadiene, styrene allyl chloride, allyl alcohol, allyl acetate, allyl ether, allyl cyanide, cyclohexenecarbonitrile, soy bean oil, cotton seed oil and the like.

Organic Hydroperoxides

The organic hydroperoxides which can be used within the scope of the instant invention are broadly any organic compounds having at least one hydroperoxide moiety but free of functional groups which are deleterious to the epoxidation reaction or are normally reactive with the hydroperoxides. A group of useful hydroperoxides is represented by the formula R'-OOH wherein R' is a hydrocarbyl or a substituted hydrocarbyl group containing from 3 to 20 carbon atoms. The hydrocarbyl group may be alkalaryl, alkyl or substituted alkyl or arylalkyl. The substituted alkyl or arylalkyl hydrocarbyl can contain oxygen incorporated into the functional group such as hydroxy, hydrocarboloxy, hydrocarboxyloxycarbonyl, hydrocarboxylocy, and the like. Additionally, the hydrocarbyl or substituted hydrocarbyl can contain halogens, e.g., chlorine, florine, bromine and iodine.

The most preferred hydroperoxides are secondary and tertiary hydroperoxides containing up to about 15 carbon atoms such as tertiary butyl hydroperoxides, tertiary amyl hydroperoxide, cyclohexene hydroperoxide, tetralin hydroperoxide, cumene hydroperoxide, diisopropyl benzenehydroperoxide, α-methyl benzylhydroperoxide, and the like.

The amount of reactants present in the reaction mixtures will generally depend upon the olefin to be epoxidized and the hydroperoxide; but generally molar ratios of olefin to hydroperoxide of from about 1:10 to 100:1 and preferably from 1:2 to 10:1 have been found sufficient. Additionally, the molar ratios of hydroperoxide to the catalyst material will likewise depend upon the boron catalyst material will likewise depend upon the boron containing substances used, the olefin, the hydroperoxide and the reaction condition. Generally molar ratios of hydroperoxide to catalyst from about 1:1 to 10,000:1 have been found sufficient, and preferably molar ratios of 1:1 to 1,000:1 are utilized.

Although it is not necessary, diluents and/or solvents which are liquid at reaction temperatures and pressures and are substantially nondeleterious under reaction conditions to the reactant and products may be utilized. Useful solvents and diluents include aliphatic or aromatic hydrocarbons, alcohols, ethers and esters. Aliphatic and aromatic halogenated hydrocarbons may also be utilized. Examples of suitable solvents include tertiary butyl alcohol, octane, cyclohexane, benzene, toluene, ethyl benzene, dichloromethane, ethylene dichloride, propylene dichloride, chlorobenzene, and the like.

Additionally, additives such as anitoxidants and inorganic bases may be added to the reaction mixture if desired. Examples of such additives are di-t-butyl-p-cresol, p-methoxyphenol, diphenylamine, sodium oxide, magnesium oxide and the like. Additives of these types are particularly useful for preventing undesirable side reactions.

The epoxidation reaction is preferably conducted in a tubular reactor equipped with an internal thermowell to which are fed two streams 50:50 peroxide-alcohol and olefin pumped as a liquid. The weight ratios of these streams vary from about 1:0.3 to 1:2. Temperatures of 90° to 130° C and pressures of 500 to 1500 psig are recommended. The liquid hourly space velocities range from 0.5 to 3 hours.

At the conclusion of the reaction, the product mixture can be separated and the product recovered by conventional methods such as fractional distillation, selective extraction, filtration, and the like. Further, the catalyst, unreacted reactants, solvents and diluents if such are used, can be recycled.

To further illustrate the process and the catalyst of the instant invention the following examples are provided not as limitation but by further way of demonstrating the details of the invention.

EXAMPLE I

This example shows typical catalyst pellet strength with 5/32 inch diameter pellets made by pilling.

| Catalyst | Composition, Wt. % | Crush Strength, Lg. | (Chatillon (Tester) |
|---|---|---|---|
| A | 5 Al-95WB | 31 | |
| B | 20 Al-80WB | 50+ | |
| C | 10 Mg-90WB | 21 | |
| D | 20 Zn-80WB | 31 | |

EXAMPLE III

Further improvement in catalyst pellet strength was obtained by heat treating formed pellets in a nonoxidizing gas stream. The crush strength of a 10 weight percent preoxidized aluminum bound tungsten boride catalyst was improved by heating the pellets in a stream of nitrogen at a temperature of 565° C.

| Catalyst | Composition, Wt. % | Crush St. Lbs. |
|---|---|---|
| E | 10 Al-90WB | 28 |
| F | 10 Al-90WB (Heated, 1050° F) | 45 |

EXAMPLE IV

For the evaluation of epoxidation activity the yield of octene-oxide was measured after a 5 hour reflux in the presence of (TBHP), octene-1, and the catalyst.

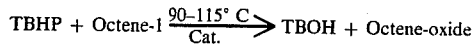

$$\text{TBHP + Octene-1} \xrightarrow[\text{Cat.}]{90-115° C} \text{TBOH + Octene-oxide}$$

In practice, 112 grams of octene-1 was charged to a tubular reactor containing 5 grams of catalyst. The flask was heated to 90° C. and 25 grams of 90% TBHP added dropwise over a 5 minute period. After 5 hours of reflux, the system was cooled to room temperature. The octene-oxide content of the liquid product was determined from Glass Chromatography analysis.

The table below demonstrates the improvement in yield of octene-oxide obtained with WB to which preoxidized powdered aluminum was added as a binding agent.

| Cat. | Cat. Composition Wt. Percent | % Yield (Basis TBHP Charged) |
|---|---|---|
| G | WB (Powder Form) | 55 |
| H | 5 Al-95WB (20 mesh) | 81 |
| I | 10 Al-90WB (20 mesh) | 82 |
| J | 5 Al-95WB (5/32" Tablets) | 61 |
| K | 10 Mg-90WB (5/32" Tablets) | 1 |
| L | 20 An-80WB (5/32" Tablets) | |

Catalysts H&I above were initially formed into 5/32 inch pellets and then crushed to 20 mesh particles. This permitted a better comparison with the powdered WB alone. (G). All the powdered samples were agitated during the reflux period. Catalyst J, K and L were evaluated in pelleted form without any agitation. The latter method is not considered an ideal way of evaluation, however, even in its pelleted form, without agitation, Catalyst J gave a higher yield of octene-oxide than WB powder alone. Also the crush strength of Catalyst J before reaction was 19 lbs. After reaction the crush strength was 39 lbs. Thus, an improvement in strength was observed.

Catalysts K&L were inactive to octene. Although the data is not shown, both were also inactive when the pellets were ground to a fine powder and evaluated.

The present invention has been disclosed herein with particular respect to certain preferred embodiments thereof. However, a latitude of modification, change and substitution is intended in the foregoing disclosure, and in some instances some compositions of the invention will be employed with different binding agents for optimum results. Accordingly, other catalyst systems encompassed by the above disclosure are fully equivalent to those claimed hereinbelow.

What is claimed is:

1. A method for the liquid phase epoxidation of an olefin having from about 2 to about 60 carbon atoms with an organic hydroperoxide comprising the steps of: reacting said olefin in a tubular reaction zone with said organic hydroperoxide at temperatures of about 90° C to about 130° C and pressures sufficient to maintain the product and reactants substantially in liquid phase; the molar ratio of olefin to hydroperoxide ranging from about 1:10 to 100:1; in the presence of a shaped catalyst consisting essentially of 80 to 95 percent by weight of finely divided particles of tungsten boride intimately bonded by 5 to 20 percent by weight of lightly preoxidized aluminum powder having an oxide coating constituting from 5 to 10 percent by volume of said powder, the molar ratios of hydroperoxide to catalyst ranging from about 1:1 to 10,000:1 and recovering the corresponding epoxy compound.

2. The process of claim 1, wherein said reaction is carried out at a liquid hourly space velocity ranging from 0.5 to 3 hours under a pressure of 500 to 1500 psig.

3. The process of claim 1, wherein the reaction is carried out in the presence of a solvent of the group of tertiary butyl alcohol, octane, cyclohexane, benzene, toluene, ethyl benzene, dichloromethane, ethylene dichloride, propylene dichloride, chlorobenzene.

* * * * *